(12) United States Patent
Lee et al.

(10) Patent No.: US 11,940,974 B2
(45) Date of Patent: Mar. 26, 2024

(54) DATABASE LOCK

(71) Applicant: Otsuka America Pharmaceutical Inc., Rockville, MD (US)

(72) Inventors: Angela Lee, Monmouth Junction, NJ (US); Padma Samala, Princeton, NJ (US); Shameka DaCosta, Bordentown, NJ (US); Indra Agarwal, Clarksburg, MD (US); Fugui Dong, Rockville, MD (US); Srikanth Gottipati, Princeton Junction, NJ (US)

(73) Assignee: OTSUKA AMERICA PHARMACEUTICAL, INC., Rockville, MD (US)

( * ) Notice: Subject to any disclaimer, the term of this patent is extended or adjusted under 35 U.S.C. 154(b) by 1095 days.

(21) Appl. No.: 16/374,697

(22) Filed: Apr. 3, 2019

(65) Prior Publication Data

US 2019/0303360 A1    Oct. 3, 2019

Related U.S. Application Data

(60) Provisional application No. 62/652,149, filed on Apr. 3, 2018.

(51) Int. Cl.
  *G06F 11/00* (2006.01)
  *G06F 11/30* (2006.01)
  (Continued)

(52) U.S. Cl.
  CPC ........ *G06F 16/2343* (2019.01); *G06F 11/302* (2013.01); *G06F 11/3065* (2013.01);
  (Continued)

(58) Field of Classification Search
  None
  See application file for complete search history.

(56) References Cited

U.S. PATENT DOCUMENTS

| | | | |
|---|---|---|---|
| 7,657,446 B1 * | 2/2010 | Houriet, Jr. | ............ G16H 15/00 705/3 |
| 9,672,580 B2 | 6/2017 | Houriet, Jr. et al. | |

(Continued)

OTHER PUBLICATIONS

Pci international Search Report and Written Opinion in International Appln. No. PCT/L152019/025670, dated May 29, 2019, 13 pages.

(Continued)

*Primary Examiner* — Tuankhanh D Phan
(74) *Attorney, Agent, or Firm* — Pillsbury Winthrop Shaw Pittman, LLP (57) ABSTRACT

Methods, systems, and apparatus, including computer programs encoded on a storage device, for monitoring the status of a database prior to locking the database. In one aspect, the method comprises receiving a request to generate a mock database, accessing a set of database lock readiness metrics, wherein the set of database lock readiness metrics include one or more attribute values that each specify a value of an attribute of database data that must be satisfied for the database to be locked, correlating information that includes (i) the set of database lock readiness metrics and (ii) database data of the database, and generating a database lock readiness report structure, based on a mock database lock representing a snapshot of the database at a particular point in time, that indicates whether each of the one or more attribute values specified by the set of database lock readiness metrics have been satisfied.

27 Claims, 3 Drawing Sheets

(51) Int. Cl.
G06F 11/34 (2006.01)
G06F 16/23 (2019.01)
G06Q 10/06 (2023.01)
G16H 10/20 (2018.01)

(52) U.S. Cl.
CPC ......... *G06F 11/3495* (2013.01); *G06Q 10/06* (2013.01); *G16H 10/20* (2018.01)

(56) References Cited

U.S. PATENT DOCUMENTS

| | | |
|---|---|---|
| 2011/0161101 A1 | 6/2011 | Liegucin et al. |
| 2012/0150802 A1* | 6/2012 | Popov .................. G06F 11/2094 707/635 |
| 2013/0132854 A1* | 5/2013 | Raleigh .................. H04W 4/60 715/738 |
| 2018/0046779 A1 | 2/2018 | Millen et al. |

OTHER PUBLICATIONS

PCT International Preliminary Report on Patentability in International Appln. No. PCT/US2019/025670, dated Oct. 6, 2020, 7 pages.

* cited by examiner

DATABASE LOCK

CROSS-REFERENCE TO RELATED APPLICATIONS

This application claims the benefit of the U.S. Provisional Patent Application No. 62/652,149 filed Apr. 3, 2018 and entitled "Database Lock," which is incorporated herein by reference in its entirety.

BACKGROUND

One of the most critical and time sensitive parts of a clinical trial is a database lock. A database lock protects the integrity by preventing unauthorized or unintentional changes to data generated during a clinical trial.

SUMMARY

According to one innovative aspect of the present disclosure, a method for monitoring the status of a database prior to locking the database is disclosed. In one aspect, a method is disclosed that can include actions of receiving, by a first computer, a request to generate a mock database lock for the database at a point in time before the database is locked, and responsive to the request to generate the mock database lock: accessing, by the first computer, a data structure stored in a first data source, wherein the data structure includes fields structuring data describing a set of database lock readiness metrics, wherein the set of database lock readiness metrics include one or more attribute values that each specify a value of an attribute of database data that must be satisfied for the database to be locked, correlating, by the first computer, information that includes (i) the data structured by the fields of the first data structure that describes the set of database lock readiness metrics and (ii) the database data of the database, wherein the data of the database is stored by a second data source, and generating, by the computer and based on the correlated information, a database lock readiness report data structure, based on a mock database lock representing a snapshot of the database at a particular point in time, that indicates whether each of the one or more attribute values specified by the set of database lock readiness metrics have been satisfied.

Other versions include corresponding systems, apparatus, and computer programs to perform the actions of method defined by instructions encoded on computer storage devices.

These and other versions may optionally include one or more of the following features. For instance, in some implementations, the first data source can include one or more memory devices of the first computer.

In some implementations, the first data source is stored remotely by a second computer. In such implementations, accessing, by the first computer, a data structure stored in the first data source can include transmitting, by the first computer, a request to the second computer for one or more database lock readiness metrics, wherein the request includes a data structure that has fields structuring data that includes an identifier of the database, and receiving, by the computer, one or more data structures that include fields structuring data that represents the set of database loss readiness metrics.

In some implementations, the second data source can include one or more memory devices located remotely from the first computer.

In some implementations, the method can further include determining, by the first computer and based on the generated lock readiness report data structure, whether the database is ready for locking, and in response to determining, based on the generated lock readiness report data structure, that the database is ready for locking, transmitting a notification to a user device indicating that the database is ready for locking.

In some implementations, the method can further include determining, by the computer and based on the generated lock readiness report data structure, whether the database is ready for locking, and in response to determining, based on the generated lock readiness report data structure, that the database is not ready for locking, identifying a person who is associated with a role to remedy attributes of the database determined to be insufficient to satisfy one or more requirements of the one or more database lock readiness metrics, and transmitting a notification to a user device of the person that includes data (i) indicating that the database is not ready for locking and (ii) including one or more instructions for preparing the database for locking.

In some implementations, generating, by the computer and based on the correlated information, a database lock readiness report data structure, based on a mock database lock, can include generating a data structure that includes, for each database lock readiness metric, a plurality of fields structuring data that describes an extent to which the database satisfies the database lock readiness metric.

In some implementations, the method can further include generating a mock database lock snapshot.

In some implementations, the database data can include database attributes describing features of a clinical trial database.

DETAILED DESCRIPTION

The database lock process in clinical trials is the process of finalizing cross functional data reviews, quality control checks and gathering documentation to support the integrity of the clinical trial database. Database lock is the action taken by data management to prevent further changes to the trial database. Database lock removes all write-access to all users and prevents data from being corrupted or invalidated after the database lock timestamp. Database lock is a milestone during a clinical trial. Further data analysis and reporting timelines are based on the database lock.

The present disclosure is related to a system and method for evaluating the state of a clinical database in advance of a clinical database lock. In one aspect, a mobile application is disclosed for clinical database lock management. The mobile application manages a database lock workflow and automates team notification and communications by implementing data structures that provide for access to various mobile contacts, pushing of alerts and notifications, generation of data structures for storing data representing time to complete various tasks, establishments over various communication protocols of real-time communication channels, generation of readiness metrics, and so forth. The present disclosure provides numerous advantages over existing systems including improved operational efficiency, increased capacity for multiple locks at the same time, reduced time to database lock, reduction of risk of missing study milestones, and study team transparency.

Figure 1:
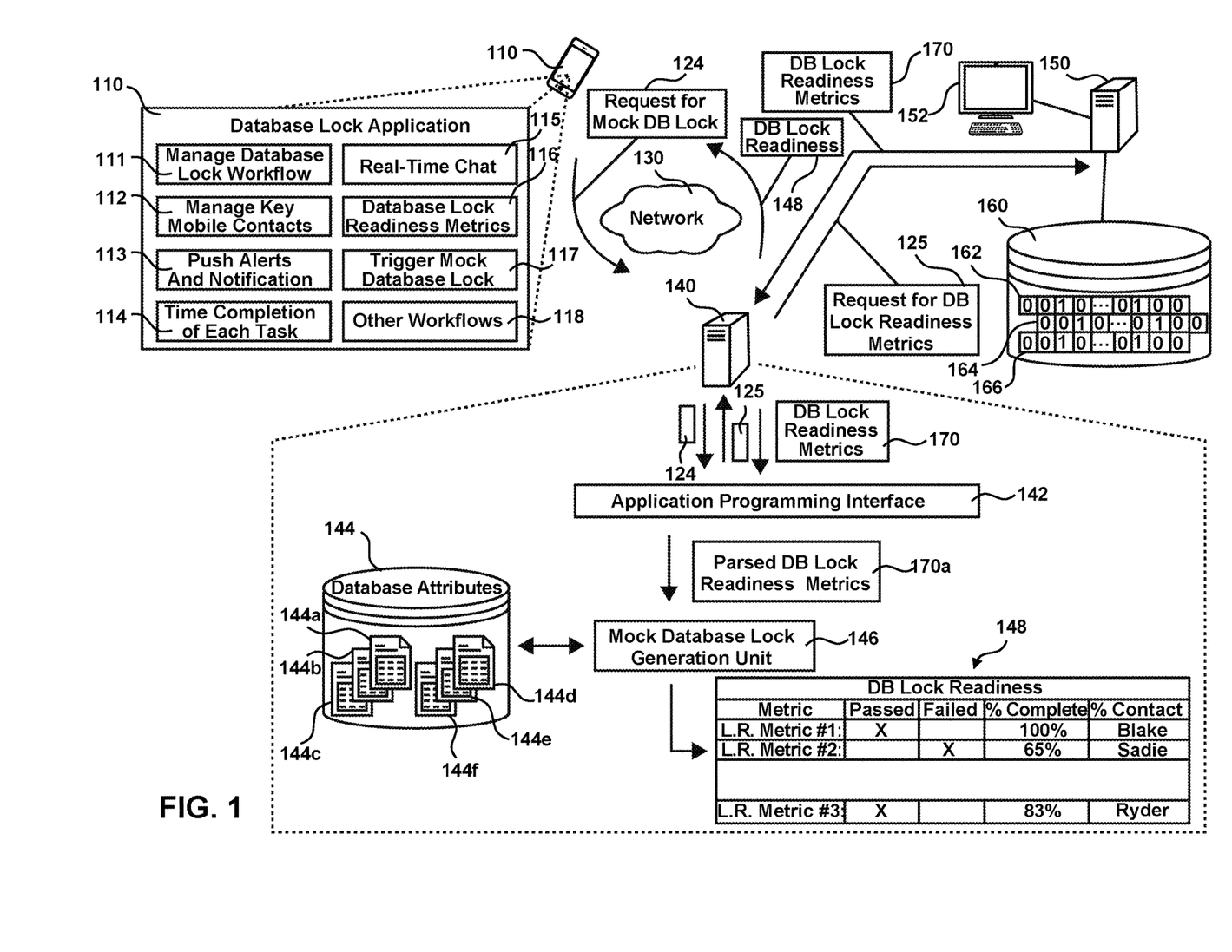
FIG. 1 is a contextual diagram of an example of a system for monitoring the status of a clinical trial database prior to locking of the clinical trial database.

FIG. 1 is a contextual diagram of an example of a system 100 for monitoring the status of a clinical trial database prior to locking of the clinical trial database. The system 100 can include a mobile device 110, an application server 140, and one or more distributed computers 150 storing a first data source 160. Though the first data source 160 is depicted as being stored by the first distributed computer 150 that is separate from the application server HO, the present disclosure need not be so limited. Instead, the data sources 150 may be a database that is stored by the application server 140.

However, certain technical advantages may be gained by using the distributed architecture of FIG. 1. For example, a user such as a clinical data manager, or other user, can use the terminal 152 to connect to the first distributed computer 150, using one or more networks, and then use the terminal to store data in the first data source 160 and retrieve data from the first data source 160 related to monitoring the clinical trial database. In such implementations, storing the data related to a clinical trial in the first distributed computer can reduce the load on the application server 140 and avoid bottlenecks at the application server 140. In some implementations, the data related to the clinical trial database that is stored in the first data source 160 can include a plurality of database lock readiness metrics 162, 164, 166. The data base lock readiness metrics may include conditions that must be satisfied prior to locking the clinical database.

The clinical trial database, itself, is not depicted by FIG. 1. In some implementations, the system of FIG. 1 may not even have direct access to the clinical trial database. Instead, database attributes 144 of the clinical trial database may be obtained and stored in the application server 140. These database attributed 144 may be obtained by syncing with one or more remote data sources. Alternatively, or in addition, one or more of the database attributes 144 such as project timelines, data describing features of the clinical trial database, or the like may be entered by one or more users of the database lock application 110a.

The user device 110 can access a database lock application 110a. The database lock application 110a can include a native software application comprised of software instructions stored in a memory device of the user device 110 that, when executed by one or more processors of the user device 110, cause functionality described the software instructions to be realized. Alternatively, in other implementations, the database lock application 110a may be a web application that is hosted by the application server 140, or other computer, and whose controls are accessed using a web browser executing on the user device 110. The database lock application 110a can be used to monitor the status of the clinical trial database to determine whether the clinical trial database is ready for locking.

Monitoring the status of a clinical trial database can include storing database attributes 144 on the application server 140 and analyzing these database attributes 144 in view of a set of database lock readiness metrics. The database attributes 144 can include a variety of data records 144a, 144b, 144c, 144d, 144e, 144f describing aspects of the clinical trial database. In some implementations, the server 140 need not directly access the clinical trial database in order to generate the set of database attributes 144. For example, the database attributes 144 may include one or more data records describing clinical trial timelines, static project timeline templates, or the like. In some implementations, these timelines may be created using modules of the database lock application 110a such as the manage database lock workflow module 111 or the time to completion of each task module 114. Alternatively, or in addition, the data attributes 144 may be imported from one or more other computers by periodically synchronizing the database attributes 144 with data describing the state of a clinical trial database. Other records describing database attributes may include data describing whether all documents have been received during the clinical trial, data describing number of queries that need to be executed during the clinical trial, or the like.

The database lock application 110 can provide access to multiple software modules for monitoring the status of a clinical trial database prior to locking of the clinical trial database. For example, the multiple software modules can include a manage database lock workflow module 111, a manage key mobile contacts modules 112, a push alerts and notifications modules 113, a time completion of each task module 114, a real-time chat module 115, a database lock readiness metrics module 116, a trigger mock database lock module 117, and an other workflows module 118.

The manage database lock workflow module 111 provides access to a software management program that enables the user to manage the database lock workflow. In some implementations, selection of an icon representing the manage database lock workflow module 111 on a graphical user interface of the user device 111 can trigger display of a series of one or more graphical user interfaces that can be used to manage a database lock workflow. Using the one or more graphical user interfaces provided by the management database lock workflow 111, the user can also access, review, create, edit, or any combination thereof, rules, policies, or the like that specify data management operations to be performed on the data generated or obtained during the clinical trial. By way of example, a user can use the database lock workflow module 111 to create, edit, or review data management operations. Data management operations may include, for example, rules, policies, or the like protecting the quality of the types of data maintained by the clinical trial database. Such rules or policies may include, for example, database user roles, edit permissions, requirements for a database lock, or the like.

A user can use the graphical user interfaces provided by the manage database lock workflow module 111 to define user roles. In some implementations, the defining a user role can also include the allocation of one or more tasks to an individual that the individual must perform to prepare the clinical trial database to be locked. For example, a user such as a clinical data manager can assign a role to another user that requires the other user to ensure that the clinical trial database complies with one or more lock readiness metrics, or milestones, with a certain degree of completeness to prepare the clinical trial database for locking.

The manage key mobile contacts module 112 can provide access to one or more graphical user interfaces that enable a user of the database lock application 110a to access contact information of other users on a clinical trial database management team. For example, selection of an icon representing the manage key mobile contacts module 112 can trigger display of one or more graphical interfaces that can provide search functionality that enables user to search contacts using a name, a phone number, an email address, a role, or the like. In some implementations, a user may be able to use the one or more graphical user interfaces of the manage key mobile contacts module 112 to search contacts based on lock readiness metrics, or milestones. For example, a user of the database lock application can provide a contact query that includes a lock readiness metric and received, from the database lock application, one or more contacts have a role that is responsible for handling the particular lock readiness metric.

The push alerts and notifications module 113 provides access to a module for generating alerts and notifications. For examples, selection of an icon representing the push alerts and notifications module 113 can trigger one display of one or more graphical user interfaces that can be used to set criteria for transmission of alerts or notifications to users who are associated with a database lock team. In some implementations, alerts and notifications may be different types of messages. For example, an alert may be a targeted message that is broadcast to one or more particular users associated with a database lock team whereas a notification may be a general message that is broadcast to all users associated with a particular database lock team. In other implementations, there may be no practical difference between alerts and notifications, and each may merely refer to an electronic message that is transmitted to one more users who is associated with a database lock team. Alerts or notifications may include, for example, smart phone notifications. The push alerts and notification module 113 can be used to set one or more criteria that, upon occurrence of the criteria, trigger transmission of the one alerts or notifications. Alternatively, the push alerts and notification module 113 can be used to transmit alerts or notifications on demand. Recipients of an alert, notification, or both, can be identified using the manage key mobile contacts module 112.

The time completion of each task module 114 can be used to manage project deadlines. For example, selection of an icon representing the time completion of each task module 114 on a graphical user interface of the user device 110 can trigger display of one or more graphical user interfaces that can be used to track and schedule deadlines. In some implementations, the time completion of each task module 114 can be used to create, edit, or review, clinical trial timelines, static project timeline templates, or the like. In some implementations, the one or more graphical user interfaces may include a display a calendar, electronic task planning tool, or the like. Using the time completion of each task module 114, assign a task to another user of a particular role, set a deadline for a task, notify a user of the task, deadline, or both. The user can review outstanding deadlines, upcoming deadlines, overdue deadlines, and take measures to keep progress towards clinical database lock on track.

The real-time chat module 115 can be used to facilitate real-time communication between users of the database lock application. For example, selection of an icon representing the real-time chat module 115 can trigger display of an instant messenger application that for communication amongst users working on management of a particular clinical trial database leading to database lock. Real-time chat allows for conversation-like communication via text that enables back and forth communication between one or more parties to occur in real-time, thereby avoiding delays in a communication pipeline.

The database lock readiness metrics module 116 allows a user to access or create database lock readiness metrics. Database lock readiness metrics may data structures stored in the data source 160 that have fields structuring data that describes one or more stored policies, rules, criteria, or milestones that must be satisfied in order for a clinical trial database such as clinical trial database to be properly locked. A clinical trial database can be properly locked when each of plurality of preconditions meet a predetermined quality threshold to establish that the data in the clinical trial database is accurate and complete. The plurality of preconditions, and their respective thresholds, can be customizable and can vary from clinical trial database to clinical trial database. For purposes of this specification, a set of preconditions that must be satisfied to achieve a proper database lock for a particular clinical trial database is defined by a set of database lock readiness metrics associated with the particular clinical trial database. Database lock readiness metrics may be clinical trial specific or general to multiple different clinical trials.

Database lock readiness metrics may be generated for any attribute of a clinical trial database and can include a criteria, policy, rule, restriction, or otherwise, that one or more values associated with the attribute must satisfy one or more quality thresholds. Such database lock readiness metrics may include whether sufficient was data received during a clinical trial, whether data processed during the clinical trial, whether queries provided during the clinical trial, whether queries processed during the clinical trial, whether queries that to be processed during the clinical trial, whether sufficient external data to be integrated into the clinical trial database, and the like. By way of example, a database lock readiness may be created that requires that 95%, or more, of the data generated during the clinical trial has been received and stored. By way of another example, a database lock readiness metric may be created that requires that 100% of outstanding queries provided during the clinical trial have been executed. Alternatively, or in addition, such database lock readiness metrics may include whether a requirement that a sufficient amount of data management operations of a particular type have been performed such as. For example, has necessary data been reviewed, reported, filtered, formatted, or the like. In some implementations, the database lock readiness metrics module 116 can be used to access a library of known database lock readiness metrics. Alternatively, the database lock readiness metrics module 116 can be used to generate database lock readiness metric data structures specify one or more of these or other rules that a clinical data manager sees fit to ensure a proper clinical database lock is achieved.

Database lock readiness metrics can be created through the database lock application 110a using the user device 110. Alternatively, database lock readiness metrics may also be generated by access another native version of the database lock application installed on the terminal 152, a web application version of the database lock application accessed using a browser installed on the terminal 152, or the like. In either event, whether the database lock readiness metrics data structures were generated using the user device 110 or the terminal 152, using the database lock application described herein, the database lock readiness metrics may be stored in the database source 160. In either scenario, the user device 110 or the terminal 152 can store the database lock readiness metric data structures in the data source 160 as database lock readiness metric data structures 162, 164, 166.

The trigger mock database lock module 117 can be used to evaluate the state of a current clinical database such as clinical database prior to locking. The evaluation of the state of the state of a current clinical database is achieved by generating a mock database lock. The mock database lock presents a snapshot of the current of a clinical trial database. The mock database lock snapshot is generated based on the database attributes 144 that describe features of the clinical trial database in view of a set of database lock readiness metrics. The mock database lock snapshot can be evaluated to determine whether the clinical trial database is ready for locking. In some implementations, evaluating the database lock snapshot may include evaluating one or more database lock readiness reports 148 generated based on the correlation of the mock database lock snapshot and one or more database lock readiness metrics. If it is determined, based on an evaluation of the mock database lock snapshot, that the clinical trial database is ready for locking, then the clinical trial database can be locked. If, alternatively, it is determined, based on an evaluation of the mock database lock snapshot, that the clinical trial database is not ready for locking, then the generated mock database lock, or one or more database lock readiness reports 148, can be evaluated to determine a set of tasks that need to be performed to get the clinical trial database ready for locking.

Selection of an icon representing the trigger mock database lock module 118 can cause the user device 110 to generate a request 124 for mock database lock to be generated. Generation of the request 124 for mock database lock can include the user device automatically, in response to the selection of the icon representing the module 118, obtaining information from a profile of the user of the user device. The obtained information can include, for example, a name of a clinical trial database, a current date and time, and the like. Generating the request 124 can include generation of a data structure that has fields structuring the name of the clinical trial database, the current data and time, a destination server identifier, a user device identifier, or the like.

The generated request 124 can be transmitted, by the user device 110, to the application server 140 using the network 130. The network 130 can include a wired Ethernet network, an optical network, a LAN, a WAN, a cellular network, the Internet, or any combination thereof. Such use of the selection of a single icon generate request that, when processed by the application server 140, causes the application server 140 to generate a mock database lock simplifies evaluation of a clinical trial database. This simplicity ensures that anyone, even a person not skilled in database administration, can trigger the creation of a mock database lock. The advantages provided by this, and other features of the database lock application 110a, improve the speed and accuracy of arriving at a database lock. Getting to database lock faster can result in significant advantages in product pipeline for products such as new drugs. For example, getting to database lock faster can result in the product getting to market faster. Thus technical improvements provided by the subject matter of the present disclosure that streamline the monitoring of clinical database can directly result in significant financial gains by enabling increasing a company's chances of being first to market with a particular product such as a new drug. These technical improvements include (i) simplicity of generating mock database locks and (ii) correlation of database lock readiness metrics and clinical database attributes of a mock database lock snapshot to identify potential deficiencies in a clinical database that need to be addressed before database lock can have significant impacts a company's revenue stream.

However, though this example uses selection of a single icon to generate a request that causes the application server 140 to generate a mock database lock, the present disclosure need not be so limited. Instead, selection of an icon generating the trigger mock database lock module 118 can trigger generation of one or more user interfaces that can include one or more fields, icons, or other controls that prompt a user for further input required to generate a mock database lock. For example, a user can be prompted to input an identifier for the clinical trial database to be evaluated, a date the mock database lock is supposed to be generated based on (e.g., mock database lock at current data and time, future data and time, or past data and time).

The application programming interface 142 of the application server 140 can receive the request 124 for mock database lock. The application programming interface 142 can generate a request 125 for database lock readiness metrics based on the received request 124 for mock database lock. The request 125 for database lock readiness metrics can include a data structure generated by the application programming interface 142 that includes fields structuring data that includes data identifying the clinical trial database identified by the request 124 for mock database lock, a destination address for the distributed computer 150, a destination address for the data source 160, an address for the application server 140, or any combination thereof.

The application server 140 can transmit the request 125 for database lock readiness metrics to location of the data source 160. If the data source 160 is maintained by a remote computers as shown in the example of FIG. 1, then the application server 140 can transmit the request 125 using one or more networks such as the network 130. Alternatively, if the data source 160 is local to the application server 140, the application server 140 can provide the request 125 to the data source 160 using one or more direct connections such as an ethernet cable, a USB cable, a USB-C cable, one or more busses, or the like. The request 125 can be executed against the data source 160 to identify one or more database lock readiness metrics 162, 164, 166, also referred to as lock readiness metrics, that are responsive to the request 125. In some implementations, database lock readiness metrics can be identified as responsive to the request 125 based on the clinical trial database identifier in the request 125.

A set of one or more database lock readiness metrics 170 responsive to the request 125 can be provided as a response to the request 125. In some implementations, the set of one or more database lock readiness metrics 170 can be received by the application programming interface 142 across one or more networks 130 from a remote distributed computer 150. In other implementations, the set of one or more database lock readiness metrics 170 can be received from one or more local sources across an ethernet cable, one or more USB cables, one or more USB-C cables, one or more busses, or the like.

The application programming interface 142 can process the received database lock readiness metrics 170 to prepare an input 170a to the mock database generation module 146. Processing the received database lock readiness metrics can include parsing the message received as response to the request 125 to extract the set of one or more database lock readiness metrics 170 from the received response. Parsing the message received as a response to the request 125 can include identifying and removing any excess information such as packet headers included in the message having database lock readiness metrics 170 that is received by the application programming interface 142. Alternatively, processing the received database lock readiness metrics may include formatting the received database lock readiness metrics for input to the mock database lock generation module. Such formatting may be determined based on the configuration of the mock database lock generation module design. However, such formatting generally includes at least generation of an input to the mock database lock generation module data that includes an identifier for the clinical trial database included in initial request 124 for mock database lock, an identifier for the lock readiness metric, minimum thresholds established by the lock reading metric for the particular clinical trial database identified by the clinical trial database identified in the initial request. The minimum thresholds would be described by fields of the database lock readiness metrics returned responsive to the request 125.

The mock database lock generation module can receive the parsed database lock readiness metrics 170 and access the clinical trial database identified by the parsed database lock readiness metrics 170. The mock database lock generation module can determine, based on the received parsed database lock readiness metrics 170a and database attributes 144 an extent to which the clinical trial database is ready for locking. Determining whether the clinical trial database is ready for locking can include generating a mock database lock based on database attributes 144 and then correlating the parsed database lock readiness metrics 170a to and the database attributes 144.

Correlating the parsed database lock readiness metrics 170a and the database lock attributes 144 can include determining whether one or more values of database attributes satisfy requirements set forth by the parsed database lock readiness metrics 170a. For example, a lock readiness metric may require that a certain threshold percentage of generated clinical data must be received and stored by the clinical trial database must be received and stored by the clinical trial database. Correlating the parsed database lock readiness metrics and the database attributes 144 can include applying a lock readiness metric filter requiring the certain threshold percentage of clinical data received to a value of one or more database attributes 144 representing the amount of clinical data receive by the clinical trial database. The mock database lock generation module 146 can generate an entry in a database lock readiness report 148 describing the extent to which this lock readiness metric has been met.

By way of another example, correlating the parsed database lock metrics 170a and the database attributes 144 can include applying lock readiness metric filter requiring the clinical database to have executed a threshold amount of queries related to the clinical trial. The mock database lock generation module 146 can generate an entry in database lock readiness report 148 describing the extent to which this lock readiness metric has been met. Such correlation of the parsed database lock readiness metrics 170a and the database attributes 144 can be performed for each policy, rule, requirement, or filter, established by a lock readiness metric provided to the mock database lock generation module 146 by the application programming interface 142.

A database lock readiness report 148 can include a data structure having multiple entries that each correspond to a particular database lock readiness metric. Each entry of the database lock readiness report 148 data structure can include a plurality of fields structuring data that describes (i) a particular lock readiness metric identifier and (ii) data describing an extent to which the clinical database at issue satisfies the particular lock readiness metric. Data describing an extent to which the clinical trial database satisfies the particular lock readiness metric can include data indicated whether the clinical trial database passed the lock readiness metric, data indicating whether the clinical trial database failed the lock readiness metric, a percentage indicating a level that the clinical trial database has completed the lock readiness metric, or any combination thereof. In some implementations, the data structure can also include fields structuring data that identifies a person who has as role of handling aspects of the clinical trial database identified by the lock readiness metric for a particular entry. In some implementations, the database lock readiness report 148 that describes the readiness of the clinical trial database for locking can be provided to the user device 110 by the application server 140 using one or more networks 130 for analysis by a human user. In other implementations, the application server can analyze the database lock readiness report 148 data structure to determine whether the clinical trial database is ready for locking.

In some implementations, the process of determining, based on the database lock readiness report 148, whether the clinical trial database is ready for locking may be automated. In such implementations, the application server 140 evaluates parameters of the database lock readiness report 148 data structure to determine whether each particular lock readiness metric has been fulfilled to certain level of completion. For example, the application server 140 can be configured to determine whether each lock readiness metric of a mock database lock has been satisfied at least a minimum level of completion. If the application server 140 determines that each lock readiness metric has satisfied at least a threshold level of completion, then the application server 140 can determine that the clinical trial database is ready for locking. Alternatively, if the application server 142 determines that one or more lock readiness metric has not satisfied at least a threshold level of completion, then the application server 142 can determine that the clinical trial database is not ready for locking. In such scenarios where the clinical trial database is not ready for locking, the application can identify the database lock team contact whose role is to prepare the clinical trial database for locking with respect to that particular lock readiness metric, and the application server 140 can notify the contact associated with the role to inform the contact that the contact needs to take necessary measures to improve the lock readiness metric to get the clinical trial database ready for locking. Such functionality streamlines the steps needed to be taken to achieve database lock and greatly reduces the amount of time necessary to arrive at a database lock, thereby improving a company's odds of being first to market with a particular product such as a drug.

With reference to the particular example of FIG. 1, the application server 142 can determine that the clinical trial database does not sufficiently comply with lock readiness metric #2. This is because the application server 140 determines that the generated database lock readiness report 148 indicates that the clinical trial database failed requirements of lock readiness metric #2. Alternatively, or in addition, the application server 140 can determine that the clinical trial database does not sufficiently comply with lock readiness metric #2 because a completion level of 65% of the requirements of lock readiness metric #2 fails to satisfy a threshold level of compliance with lock readiness metric #2. In such a scenario, the application server 140 can generate data for output by the user device 110 indicating that the clinical trial database is not ready for locking. The application server 140 can provide the generated data for output by the user device 110.

In some implementations, the application server 140 can also generate one or more messages for transmission to Sadie, whom is responsible for making sure that the clinical trial database is ready for locking. The message may include an alert, notification, email, or real-time communication to Sadie to inform Sadie that action needs to be taken to better prepare the clinical trial database for locking.

Figure 2:
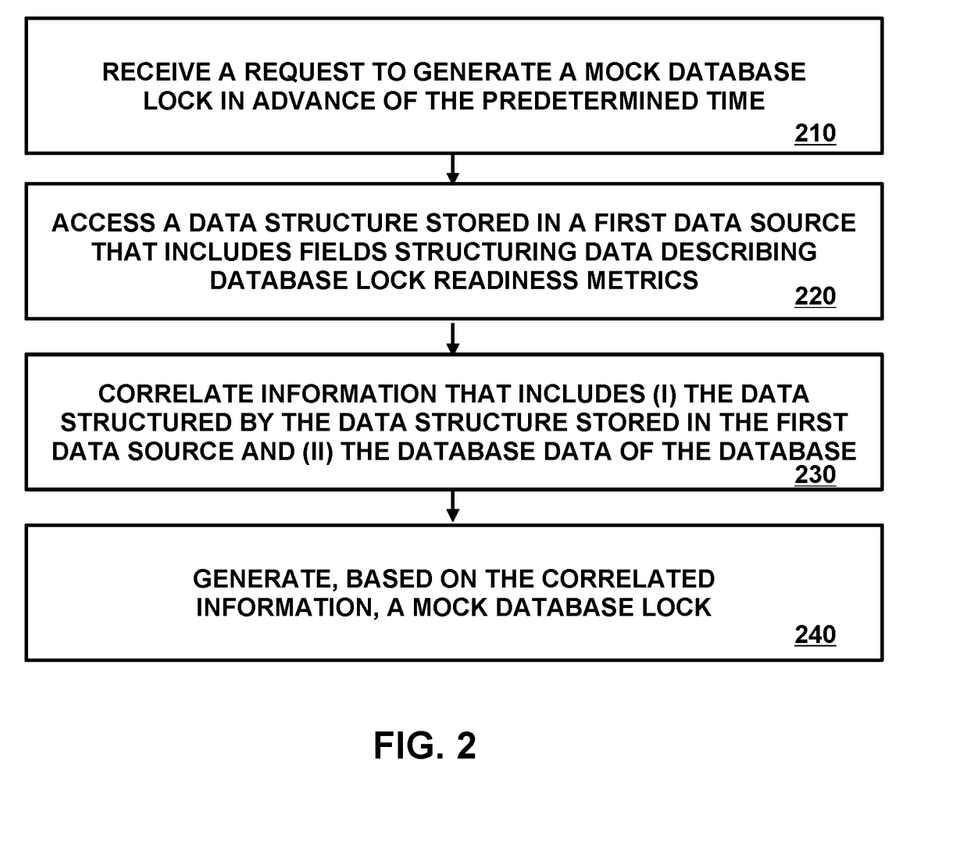
FIG. 2 is a flowchart of an example of a process for monitoring the status of a clinical trial database prior to locking of the clinical trial database.

FIG. 2 is a flowchart of an example of a process 200 for monitoring the status of a clinical trial database prior to locking of the clinical trial database. In some implementations, the process 200 can include receiving, by the computer, a request to generate a mock database lock for the database at a point in time before the database is locked (210), responsive to the request to generate the mock database lock: accessing, by a computer, a data structure stored in a first data source, wherein the data structure includes fields structuring data describing a set of database lock readiness metrics, wherein the set of database lock readiness metrics include one or more attribute values that each specify a value of an attribute of database data that must be satisfied for the database to be locked (220), correlating, by the computer, information that includes (i) the data structured by the fields of the first data structure that describes the set of database lock readiness metrics and (ii) the database data of the database, wherein the data of the database is stored by a second data source (230), and generating, by the computer and based on the correlated information, a database lock readiness report data structure based on a mock database lock representing a snapshot of the database at a particular point in time that indicates whether each of the one or more attribute values specified by the set of database lock readiness metrics have been satisfied (240).

Figure 3:
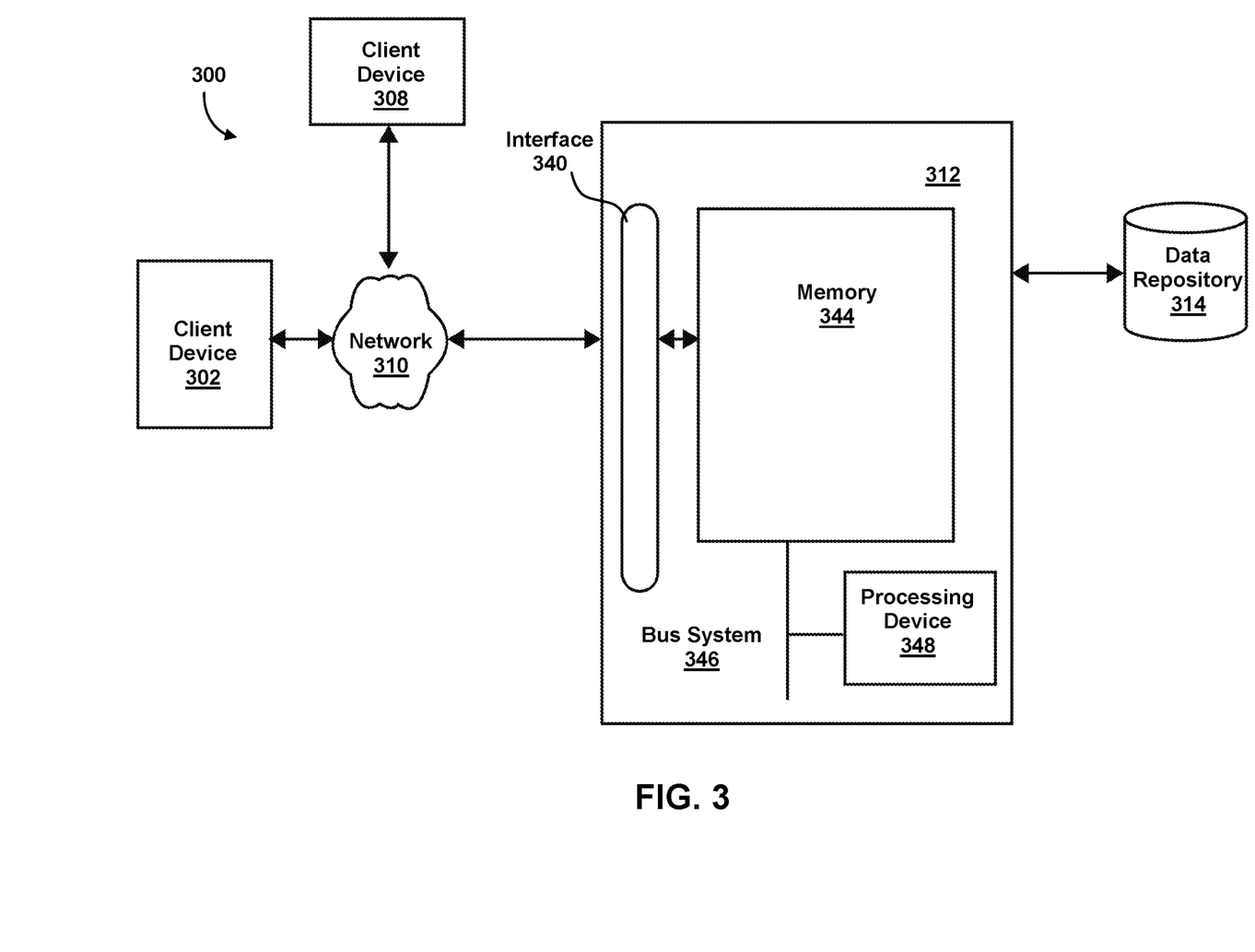
FIG. 3 is a block diagram of an example of a system for monitoring the status of a clinical trial database prior to locking of the clinical trial database.

FIG. 3 is a block diagram of an example of a system for monitoring the status of a clinical trial database prior to locking of the clinical trial database. In FIG. 3, client devices 302, 308 can be any sort of computing devices capable of taking input from a user and communicating over network 310 with server 312 and/or with other client devices. For example, client devices 302, 308 can be mobile devices, desktop computers, laptops, cell phones, personal digital assistants ("PDAs"), servers, embedded computing systems, and so forth.

In an example, the client devices 302 and 308 are configured to present one or more graphical users interfaces to their respective users. In a particular example, the client devices 302 and 308 have been installed with an application or other executable code. The application or executable code can cause presentation of the graphical user interfaces when the application or executable code is executed, e.g., by a processing device 348. These graphical user interfaces allow users to enter information and interact with other users of the system 300 and view the database lock metrics and the graphical user interfaces described herein. Particular examples of graphical user interfaces are described in more detail below.

Server 312 can be any of a variety of computing devices capable of receiving data, such as a server, a distributed computing system, a desktop computer, a laptop, a cell phone, a rack-mounted server, and so forth. Server 312 may be a single server or a group of servers that are at a same location or at different locations.

In general, the server 312 can serve as platform for the system 300 whereby users can connect with each other and share information related to their recovery status and/or provide ratings and recommendations regarding particular medical service providers. In an example, each of the client devices 302 and 308 can communicate with the server 312 and provide data indicative of a recovery log or other status updates to the server 312.

The illustrated server 312 can receive data from client devices 302, 308 via input/output ("I/O") interface 340. I/O interface 340 can be any type of interface capable of receiving data over a network, such as an Ethernet interface, a wireless networking interface, a fiber-optic networking interface, a modem, and so forth. Server 312 also includes a processing device 348 and memory 344. A bus system 346, including, for example, a data bus and a motherboard, can be used to establish and to control data communication between the components of server 312.

The illustrated processing device 348 may include one or more microprocessors. Generally, processing device 348 may include any appropriate processor and/or logic that is capable of receiving and storing data, and of communicating over a network (not shown). Memory 344 can include a hard drive and a random access memory storage device, such as a dynamic random access memory, or other types of non-transitory machine-readable storage devices. Memory 344 stores computer programs (not shown) that are executable by processing device 348 to perform the techniques described herein. Memory also stores executable logic that is executable by processing device 348 to implement to mock database lock and to implement the other functionality described herein.

Embodiments can be implemented in digital electronic circuitry, or in computer hardware, firmware, software, or in combinations thereof. Apparatus of the invention can be implemented in a computer program product tangibly embodied or stored in a machine-readable storage device for execution by a programmable processor; and method actions can be performed by a programmable processor executing a program of instructions to perform functions of the invention by operating on input data and generating output. The invention can be implemented advantageously in one or more computer programs that are executable on a programmable system including at least one programmable processor coupled to receive data and instructions from, and to transmit data and instructions to, a data storage system, at least one input device, and at least one output device. Each computer program can be implemented in a high-level procedural or object oriented programming language, or in assembly or machine language if desired; and in any case, the language can be a compiled or interpreted language.

Suitable processors include, by way of example, both general and special purpose microprocessors. Generally, a processor will receive instructions and data from a read-only memory and/or a random access memory. Generally, a computer will include one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD ROM disks. Any of the foregoing can be supplemented by, or incorporated in, ASICs (application-specific integrated circuits).

Other embodiments are within the scope and spirit of the description claims. Due to the nature of software, functions described above can be implemented using software, hardware, firmware, hardwiring, or combinations of any of these. Features implementing functions may also be physically located at various positions, including being distributed such that portions of functions are implemented at different physical locations.

The invention claimed is:

1. A method for monitoring the status of a database prior to locking the database, the method comprising:

receiving, by a first computer, a request to generate a mock database lock for the database at a point in time before the database is locked; and responsive to the request to generate the mock database lock:
  accessing, by the first computer, a data structure stored in a first data source, wherein the data structure includes fields structuring data describing a set of database lock readiness metrics, wherein the set of database lock readiness metrics include one or more attribute values that each specify a value of an attribute of database data that must be satisfied for the database to be locked;
  correlating, by the first computer, information that includes (i) the data structured by the fields of the first data structure that describes the set of database lock readiness metrics and (ii) the database data, wherein the database data is stored by a second data source and includes respective values corresponding to the set of database lock readiness metrics; and
  generating, by the computer and based on the correlated information, a mock database lock representing a snapshot of the database at a particular point in time, the snapshot having a data structure that stores:
    the set of database lock readiness metrics,
    the respective values corresponding to the database lock readiness metrics at the particular point in time,
    at least a first indication that a first respective attribute value specified by a first database lock readiness metric, from among the database lock readiness metrics, has been satisfied and is ready for locking, and
    at least a second indication that a second respective attribute value specified by a second database lock readiness metric, from among the set of database lock readiness metrics, has not been satisfied and is not ready for locking.

2. The method of claim 1, wherein the first data source includes one or more memory devices of the first computer.

3. The method of claim 1, wherein the first data source is stored remotely by a second computer, and wherein accessing, by the first computer, a data structure stored in the first data source comprises:
  transmitting, by the first computer, a request to the second computer for one or more database lock readiness metrics, wherein the request includes a data structure that has fields structuring data that includes an identifier of the database; and
  receiving, by the computer, one or more data structures that include fields structuring data that represents the set of database lock readiness metrics.

4. The method of claim 1, wherein the second data source includes one or more memory devices located remotely from the first computer.

5. The method of claim 1, the method further comprising:
  determining, by the first computer and based on the generated mock database lock, whether the database is ready for locking; and
  in response to determining that the database is ready for locking, transmitting a notification to a user device indicating that the database is ready for locking.

6. The method of claim 1, further comprising:
  determining, by the computer and based on the generated mock database lock, whether the database is ready for locking; and
  in response to determining, based on the generated mock database lock, that the database is not ready for locking:
    identifying a person who is associated with a role to remedy attributes of the database determined to be insufficient to satisfy one or more requirements of the one or more database lock readiness metrics, and
    transmitting a notification to a user device of the person that includes data (i) indicating that the database is not ready for locking and (ii) including one or more instructions for preparing the database for locking.

7. The method of claim 1, wherein generating, by the computer and based on the correlated information, a mock database lock includes generating a data structure that includes, for each database lock readiness metric, a plurality of fields structuring data that describes an extent to which the database satisfies the database lock readiness metric.

8. The method of claim 1, wherein the mock database lock is generated prior to locking the database, the method further comprising:
  locking the database after generation of the mock database lock when the mock database lock indicates that the database is ready for locking.

9. The method of claim 1, wherein the database data includes database attributes describing features of a clinical trial database.

10. A system for monitoring the status of a database prior to locking the database, the system comprising:
  one or more processors of a first computer; and
  one or more storage devices, the one or more storage devices storing instructions that, when executed by the one or more processors, cause the one or more processors to:
    receive a request to generate a mock database lock for the database at a point in time before the database is locked; and
    responsive to the request to generate the mock database lock:
      access a data structure stored in a first data source, wherein the data structure includes fields structuring data describing a set of database lock readiness metrics, wherein the set of database lock readiness metrics include one or more attribute values that each specify a value of an attribute of database data that must be satisfied for the database to be locked;
      correlate information that includes (i) the data structured by the fields of the first data structure that describes the set of database lock readiness metrics and (ii) the database data, wherein the database data is stored by a second data source and includes respective values corresponding to the set of database lock readiness metrics; and
      generate based on the correlated information, a mock database lock representing a snapshot of the database at a particular point in time, the snapshot having a data structure that stores:
      the set of database lock readiness metrics,
      the respective values corresponding to the database lock readiness metrics at the particular point in time,
      at least a first indication that a first respective attribute value specified by a first database lock readiness metric, from among the database lock readiness metrics, has been satisfied and is ready for locking, and
      at least a second indication that a second respective attribute value specified by a second database lock readiness metric, from among the set of database lock readiness metrics, has not been satisfied and is not ready for locking.

11. The system of claim 10, wherein the first data source includes one or more memory devices of the first computer.

12. The system of claim 10, wherein the first data source is stored remotely by a second computer, and wherein to access a data structure stored in the first data source, the one or more processors are further caused to:
   transmit a request to the second computer for one or more database lock readiness metrics, wherein the request includes a data structure that has fields structuring data that includes an identifier of the database; and
   receive one or more data structures that include fields structuring data that represents the set of database lock readiness metrics.

13. The system of claim 10, wherein the second data source includes one or more memory devices located remotely from the first computer.

14. The system of claim 10, wherein the one or more processors are further cause to:
   determine, based on the generated mock database lock, whether the database is ready for locking; and
   in response to a determination that the database is ready for locking, transmit a notification to a user device indicating that the database is ready for locking.

15. The system of claim 10, wherein the one or more processors are further cause to:
   determine based on the generated mock database lock whether the database is ready for locking; and
   in response to a determination, based on the generated mock database lock, that the database is not ready for locking:
      identify a person who is associated with a role to remedy attributes of the database determined to be insufficient to satisfy one or more requirements of the one or more database lock readiness metrics, and
      transmit a notification to a user device of the person that includes data (i) indicating that the database is not ready for locking and (ii) including one or more instructions for preparing the database for locking.

16. The system of claim 10, wherein to generate a mock database lock, the one or more processors are further to:
   generate a data structure that includes, for each database lock readiness metric, a plurality of fields structuring data that describes an extent to which the database satisfies the database lock readiness metric.

17. The system of claim 10, wherein the mock database lock is generated prior to locking the database, and wherein the one or more processors are further to:
   lock the database after generation of the mock database lock when the mock database lock indicates that the database is ready for locking.

18. The system of claim 10, wherein the database data includes database attributes describing features of a clinical trial database.

19. A computer-readable storage device having stored thereon instructions, which, when executed by data processing apparatus, cause the data processing apparatus to:
   receive a request to generate a mock database lock for the database at a point in time before the database is locked; and
   responsive to the request to generate the mock database lock:
      access a data structure stored in a first data source, wherein the data structure includes fields structuring data describing a set of database lock readiness metrics, wherein the set of database lock readiness metrics include one or more attribute values that each specify a value of an attribute of database data that must be satisfied for the database to be locked;
      correlate information that includes (i) the data structured by the fields of the first data structure that describes the set of database lock readiness metrics and (ii) the database data, wherein the database data is stored by a second data source and includes respective values corresponding to the set of database lock readiness metrics; and
      generate based on the correlated information, a mock database lock representing a snapshot of the database at a particular point in time, the snapshot having a data structure that stores:
         the set of database lock readiness metrics,
         the respective values corresponding to the database lock readiness metrics at the particular point in time,
         at least a first indication that a first respective attribute value specified by a first database lock readiness metric, from among the database lock readiness metrics, has been satisfied and is ready for locking, and
         at least a second indication that a second respective attribute value specified by a second database lock readiness metric, from among the set of database lock readiness metrics, has not been satisfied and is not ready for locking.

20. The computer-readable storage device of claim 19, wherein the first data source includes one or more memory devices of the data processing apparatus.

21. The computer-readable storage device of claim 19, wherein the first data source is stored remotely by a second computer, and wherein to access a data structure stored in the first data source, the data processing apparatus is further caused to:
   transmit a request to the second computer for one or more database lock readiness metrics, wherein the request includes a data structure that has fields structuring data that includes an identifier of the database; and
   receive one or more data structures that include fields structuring data that represents the set of database lock readiness metrics.

22. The computer-readable storage device of claim 19, wherein the second data source includes one or more memory devices located remotely from the data processing apparatus.

23. The computer-readable storage device of claim 19, wherein the data processing apparatus is further caused to:
   determine, based on the generated mock database lock, whether the database is ready for locking; and
   in response to a determination that the database is ready for locking, transmit a notification to a user device indicating that the database is ready for locking.

24. The computer-readable storage device of claim 19, wherein the data processing apparatus is further caused to:
   determine based on the generated mock database lock whether the database is ready for locking; and
   in response to a determination, based on the generated mock database lock, that the database is not ready for locking:
      identify a person who is associated with a role to remedy attributes of the database determined to be insufficient to satisfy one or more requirements of the one or more database lock readiness metrics, and
      transmit a notification to a user device of the person that includes data (i) indicating that the database is not ready for locking and (ii) including one or more instructions for preparing the database for locking.

25. The computer-readable storage device of claim 19, wherein to generate the mock database lock, the data processing apparatus is caused to: generate a data structure that includes, for each database lock readiness metric, a plurality of fields structuring data that describes an extent to which the database satisfies the database lock readiness metric.

26. The computer-readable storage device of claim 19, wherein the mock database lock is generated prior to locking the database, and wherein the data processing apparatus is further caused to:
   lock the database after generation of the mock database lock when the mock database lock indicates that the database is ready for locking.

27. The computer-readable storage device of claim 19, wherein the database data includes database attributes describing features of a clinical trial database.

\* \* \* \* \*